United States Patent [19]  [11]  4,303,588
Okabe et al.  [45]  Dec. 1, 1981

[54] FARNESYLACETIC ACID AMIDES

[75] Inventors: Susumu Okabe, Kyoto; Yoshiaki Omura, Okayama; Yoichi Ninagawa; Yoshiji Fujita, both of Kurashiki, all of Japan

[73] Assignee: Kuraray Co., Ltd., Kurashiki, Japan

[21] Appl. No.: 132,408

[22] Filed: Mar. 21, 1980

[30] Foreign Application Priority Data

Mar. 28, 1979 [JP] Japan .................................. 54-37585

[51] Int. Cl.³ ........................ C11C 3/00; A61K 31/16; C07D 211/22
[52] U.S. Cl. .................................. 260/404.5; 544/400; 546/235; 546/244; 546/247; 424/267; 424/250; 424/274
[58] Field of Search .............................. 544/402, 400; 260/404.5 PA; 546/235, 244, 247

[56] References Cited

U.S. PATENT DOCUMENTS 3,646,036  2/1972  Laos ..................................... 544/386

FOREIGN PATENT DOCUMENTS 122293  9/1927  Switzerland ......................... 546/247
892593  3/1962  United Kingdom ................ 546/247

Primary Examiner—Anton H. Sutto
Attorney, Agent, or Firm—Barry Kramer

[57] ABSTRACT

Novel farnesylacetic acid amide compounds represented by general formula

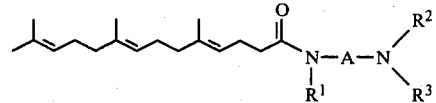

wherein A is alkylene of at least 2 carbon atoms, $R^1$ is H or lower alkyl, and $R^2$ and $R^3$ are each independently H, alkyl, cycloalkyl, alkenyl, aryl or aralkyl, or either one of $R^2$ and $R^3$ is such a group that forms, together with A, a piperidine or pyrrolidine ring which contains as constituent thereof the nitrogen atom lying therebetween, or $R^2$ and $R^3$ combinedly represent a group which forms, together with the nitrogen atom to which they are bonded, a piperidine, pyrrolidine or piperazine ring; and salts thereof have antiulcerogenic and antibacterial activities.

10 Claims, No Drawings

FARNESYLACETIC ACID AMIDES

BACKGROUND OF THE INVENTION

1. Field of the Invention

This invention relates to novel farnesylacetic acid amide compounds containing an amine nitrogen in the amine residue thereof and salts thereof.

2. Description of the Prior Art

Known farnesylacetic acid amide compounds are represented by the following formula:

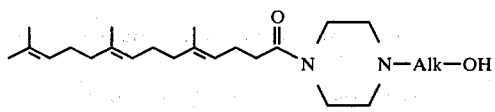

where Alk represents a lower alkylene group having at least two carbon atoms. According to U.S. Pat. No. 3,646,036, in which the above compounds are disclosed, said compounds are useful as antiulcerogenic, antiprotozoal, anthelmintic and antispasmodic agents.

SUMMARY OF THE INVENTION

According to the present invention, there are provided farnesylacetic acid amide compounds represented by the following general formula (I):

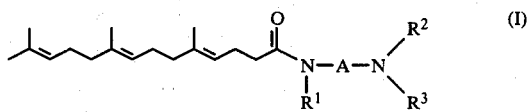

wherein A is a straight or branched alkylene group containing at least 2 carbon atoms, $R^1$ is a hydrogen atom or a lower alkyl group, and $R^2$ and $R^3$ are each independently a hydrogen atom or an alkyl, cycloalkyl, alkenyl, aryl or aralkyl group or either one of $R^2$ and $R^3$ is such a group that forms, together with A, a piperidine or pyrrolidine ring which contains as a constituent thereof the nitrogen atom lying therebetween, or $R^2$ and $R^3$ combinedly represent a group which forms, together with the adjacent nitrogen atom, a piperidine, pyrrolidine or piperazine ring. The compounds may be in the form of salts which amine-nitrogen-containing compounds can generally take, preferably in the form of pharmaceutically acceptable salts such as hydrochloride, hydrobromide, sulfate, phosphate, citrate and quaternary ammonium salts. Thus, the term "farnesylacetic acid amide compounds" as used herein shall include not only the amide compounds themselves but also salts thereof.

The farnesylacetic acid amide compounds provided by the present invention generally show strong antibacterial activity and therefore are useful as preservatives, disinfectants, germicides and fungicides. They have also antiulcerogenic activity and can be useful as anti-gastric-ulcer agents. When in the form of salts, the compounds show good affinity to water and to organic substances and therefore they can be used as surfactants or wetting agents.

DETAILED DESCRIPTION OF THE INVENTION

In general formula (I), the alkylene group represented by A may be represented more concretely by the formula

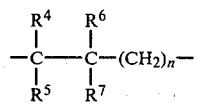

wherein $R^4$, $R^5$, $R^6$ and $R^7$ are each a hydrogen atom or a lower alkyl group such as methyl, ethyl, isopropyl, n-propyl or n-butyl, or any one of them forms, together with $R^2$ or $R^3$ in formula (I), a piperidine or pyrrolidine ring which contains as a constituent thereof the nitrogen atom to which $R^2$ and $R^3$ are bonded, and n is an integer of 0 or 1. Appropriately, the number of carbon atoms in the alkylene group should not exceed 10 and is preferably not more than 6. This should preferably be taken into consideration in the selection of each lower alkyl group $R^4$, $R^5$, $R^6$ or $R^7$ and the integer n. However, in cases where one of groups $R^4$, $R^5$, $R^6$ and $R^7$ forms, together with $R^2$ or $R^3$, a piperidine or pyrrolidine ring, the number of carbon atoms in the relevant group is not included in the number of carbon atoms in the alkylene group.

Examples of the lower alkyl group represented by $R^1$ in general formula (I) are methyl, ethyl, isopropyl, n-propyl and n-butyl. However, $R^1$ is most preferably a hydrogen atom or a methyl group. $R^2$ and $R^3$ each may be a hydrogen atom, a lower alkyl group such as the one mentioned in relation to $R^1$, a relatively higher alkyl such as n-octyl or n-decyl, a cycloalkyl group such as cyclopentyl, cyclohexyl or methylcyclohexyl, an alkenyl group such as vinyl, prenyl, geranyl or farnesyl, an aryl group such as phenyl, tolyl or xylyl, or an aralkyl group such as benzyl or phenylethyl. The number of carbon atoms contained in these hydrocarbon residues $R^2$ and $R^3$ should preferably be not more than 15. Either one of $R^2$ and $R^3$ may also be such a group that forms, together with A, a piperidine or pyrrolidine ring containing as a constituent thereof the nitrogen atom lying therebetween. Furthermore, $R^2$ and $R^3$ may combinedly form, together with the nitrogen atom to which they are bonded, a piperidine, pyrrolidine or piperazine ring. Preferably, $R^2$ and $R^3$ are each independently selected from the group consisting of a hydrogen atom, a methyl group and an ethyl group or $R^2$ and $R^3$ combinedly form a constituent of a piperidine, pyrrolidine or piperazine ring.

The amine-nitrogen-containing farnesylacetic acid amide compounds of the present invention can be prepared by any of conventional methods known per se for the preparation of known carboxylic acid amides. The most common method involves the reaction of a farnesylacetic acid or a functional or reactive derivative thereof represented by the formula

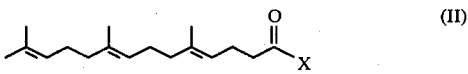

wherein X is a group capable of forming an amide bonding upon reaction with an amino group, such as OH, a halogen atom or an alkoxy group, with an amine represented by the formula

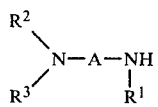   (III)

wherein A, R$^1$, R$^2$ and R$^3$ are as defined for formula (I). When the amides of formula (I) produced by the above reaction are reacted with inorganic or organic acids or alkyl halides, the corresponding salts including quaternary ammonium salts can be prepared.

For some farnesylacetic acid amide compounds of the present invention, there exist geometric isomers and/or optical isomers. The present invention includes those isomers without specifically defining the same.

Examples of the farnesylacetic acid amide compounds and salts thereof of the present invention are listed below. The compound numbers in the list will be used hereinafter to denote the compounds given those respective numbers. In the chemical formulas, the symbols F-, G- and P- represent farnesyl

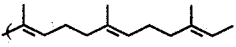, geranyl 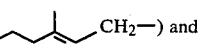 and prenyl , respectively.

(1) F—CH$_2$CONHCH$_2$CH$_2$N(CH$_3$)$_2$
 and its hydrochloride and hydrobromide,
(2) F—CH$_2$CONHCH$_2$CH$_2$N$^\oplus$(CH$_3$)$_3$.Cl$^\ominus$
(3) F—CH$_2$CONHCH$_2$CH$_2$N(C$_2$H$_5$)$_2$
 and its hydrochloride and hydrobromide,
(4) F—CH$_2$CONHCH$_2$CH$_2$N$^\oplus$(C$_2$H$_5$)$_3$.Br$^\ominus$

and its hydrochloride and hydrobromide,
(6) F—CH$_2$CONHCH$_2$CH$_2$N(G)$_2$
 and its hydrochloride and hydrobromide,
(7) F—CH$_2$CONHCH$_2$CH$_2$N(P)$_2$
 and its hydrochloride and hydrobromide,
(8) F—CH$_2$CONHCH$_2$CH$_2$CH$_2$N(CH$_3$)$_2$
 and its hydrochloride and hydrobromide,
(9) F—CH$_2$CONHCH$_2$CH$_2$CH$_2$N$^\oplus$(CH$_3$)$_3$.Cl$^\ominus$
(10) F—CH$_2$CONHCH$_2$CH$_2$CH$_2$N(C$_2$H$_5$)$_2$
 and its hydrochloride and hydrobromide,
(11) F—CH$_2$CONHCH$_2$CH$_2$CH$_2$N$^\oplus$(C$_2$H$_5$)$_3$.Br$^\ominus$

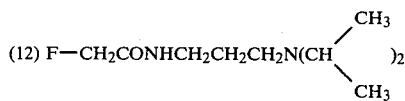

and its hydrochloride and hydrobromide,
(13) F—CH$_2$CONHCH$_2$CH$_2$CH$_2$N(G)$_2$
 and its hydrochloride and hydrobromide,
(14) F—CH$_2$CONHCH$_2$CH$_2$CH$_2$N(P)$_2$
 and its hydrochloride and hydrobromide,

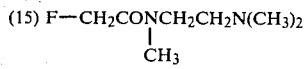

and its hydrochloride and hydrobromide,

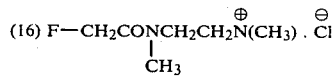

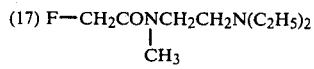

and its hydrochloride and hydrobromide,

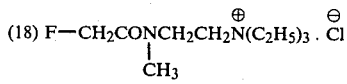

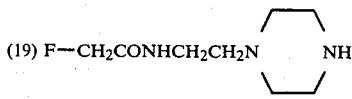

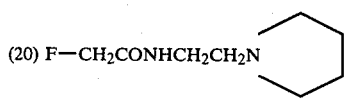

and its hydrochloride and hydrobromide,

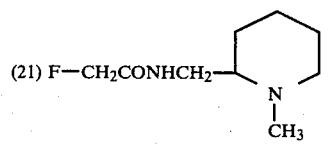

and its hydrochloride and hydrobromide,

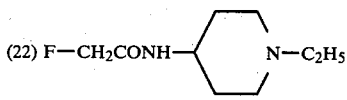

and its hydrochloride and hydrobromide,

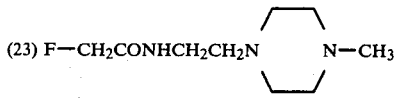

and its hydrochloride and hydrobromide,

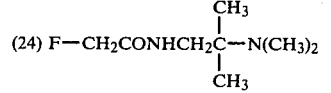

and its hydrochloride and hydrobromide,

(25) F—CH$_2$CONHCH$_2$CH$_2$NH$_2$ and its hydrochloride and hydrobromide.

As mentioned previously, the farnesylacetic acid amide compounds of the present invention have an antiulcerogenic activity and some of them are significantly more active than geranyl farnesylacetate which is currently in wide use as an antiulcer agent, as shown by the following test results.

Antiulcerogenic Activity Against Indomethacin-Induced Ulcer

After fasting for 24 hours, male Donryu rats weighing 210 to 230 grams were subcutaneously administered indomethacin suspended in a 1% carboxymethyl-cellulose solution at a dose of 20 mg/kg. After 7 hours, the rats were sacrificed with ether and the indomethacin-induced ulcers appearing on the gastric mucosa were measured for their length in mm. The total length of ulcers per animal was designated as the ulcer index. The test compounds and geranyl farnesylacetate were orally administered 10 minutes prior to the indomethacin administration. The inhibition percentages were calculated by dividing the difference in ulcer index between the dosed group and the control group by the ulcer index for the control group. The results are shown in Table 1.

TABLE 1

| Test compound | Dose (mg/kg) | Number of animals | % Inhibition |
|---|---|---|---|
| Control | 0 | 0 | — |
| (Geranyl farnesylacetate) | 300 | 20 | 6.1 |
| Hydrochloride of compound (1) | 300 | 10 | 92.4 |
| Hydrochloride of compound (8) | 300 | 10 | 98.4 |

The antiulcer agents which contain as active ingredient a farnesylacetic amide represented by formula (I) or a pharmaceutically acceptable salt thereof in accordance with the invention may take the form of tablets, capsules, powder, granules, lozenges, or liquid preparation such as sterilized solution or suspension for oral or parenteral administration. Tablets, granules and powder are suitable dosage forms for orally administering the active ingredient of the present invention. Granules and powder may optionally take the form of capsules as unit dosage form. Solid preparations for oral administration may contain conventional diluents (e.g. silicic anhydride, synthetic aluminosilicate, lactose, sugar, corn starch, microcrystalline cellulose), binders (e.g. gum arabic, gelatin, polyvinylpyrrolidone), lubricants (e.g. magnesium stearate, talc, silica), disintegrators (e.g. potato starch, carboxymethylcellulose calcium) and wetting agents (e.g. polyethylene glycol, sorbitan monooleate, sodium laurylsulfate). Tablets may be coated in a conventional manner. Liquid preparations for oral administration may be in the form of aqueous or oleaginous suspensions, solutions, syrups or the like, or they may be dried preparations to be dissolved or dispersed in appropriate vehicles prior to use. Such liquid preparations may contain those emulsifiers (e.q. lecithin, sorbitan monooleate), auxiliaries to emulsifiers (e.g. sorbitol syrup, methylcellulose, gelatin), nonaqueous vehicles (e.g. coconut oil, peanut oil), antioxidants, coloring agents, flavoring substances, and so on that are usual in the art. Liquid preparations for parenteral administration may be prepared by dissolving or suspending the farnesylacetic acid ester derivative of formula (I) in a sterile vehicle. Solutions are prepared by dissolving the active compound in a vehicle for injection, filtering and sterilizing the solution and filling ampules with the sterile solution followed by sealing hermetically. It is preferable in this case to add such auxiliaries as local anesthetic, preservative and buffer to the vehicle. Suspensions may be prepared substantially in the same manner as in the preparation of solutions except that the active compound is not dissolved but suspended in a vehicle and some other sterilizing procedure than filtration is used.

The pharmaceutical composition of the present invention which contains the farnesylacetic amide compound is effective for therapy and/or prophylaxis of ulcers of the human digestive tract, especially the gastric ulcer. The effective amount or dose of said compound depends on severity of the ulcer, physical constitution of the patient, kind of the compound of formula (I) and other factors. Generally, however, the daily dose for human adults is in the range of about 100 mg to about 2,500 mg.

Furthermore, as mentioned previously, the compounds of the present invention have an antibacterial activity and are useful as active ingredients in antibacterial agents including disinfectants, preservatives and agricultural/horticultural pesticides. Said compounds also have a surfactant activity and are suitable as ingredients in soap, shampoo and rinse, too. A test example demonstrating the antibacterial activity is shown below.

Antibacterial Activity Test

Compounds of the present invention were each diluted with acetone to specified concentrations. Paper discs, 8 mm in diameter, were soaked with the resulting solutions and then allowed to stand. After complete evaporation of the acetone, the discs were placed on bouillon agar plates (pH 7.2) containing test organisms. The test organisms Psl and X were incubated at 30° C. for 24 hours and the other test organisms at 37° C. for 24 hours. After the incubation, the radii (mm) of inhibitory zones were measured. The results are shown in Table 2. The following abbreviations were used for identification of the test organisms used.

TABLE 2

| Compound | Conc % | a | b | c | Sal | Ps | Er | Psl | X |
|---|---|---|---|---|---|---|---|---|---|
| Hydrochloride of (1) | 1 | 15A | 15A | 12A | 12B | 12C | — | | |
| | 0.1 | 11A | 12A | 10A | 10B | +C | — | | |
| Hydrochloride of (8) | 1 | 13B | 16A | 12A | 12B | 12C | — | | |
| | 0.1 | 10A | 12A | 10A | 10B | — | — | | |
| (1) | 10 | 16B | 16A | 12A | 11B | 12C | 13A | | |
| | 1 | 14B | 15A | 11A | 10B | 11C | 12A | | |
| | 0.1 | 11B | 13A | 10A | 10B | +C | — | | |
| (8) | 10 | 17A | 18A | 13A | 13B | 10C | 14A | | |
| | 1 | 13A | 15A | 12A | 13B | +C | 13A | | |
| | 0.1 | 10A | 11A | 10A | 11B | — | 11A | | |
| Hydrochloride of (15) | 1 | 15A | 18A | 15A | 14B | 15C | 22A | 21A | 23A |
| | 0.1 | 12A | 12A | 12A | 12B | — | 12A | 14A | 16A |
| Hydrochloride of (10) | 1 | 15A | 18A | 14A | 15B | 13C | 30A | 24A | 27A |
| | 0.1 | 11A | 12A | 12A | 11B | — | 18A | 16A | 16A |
| (9) | 10 | 27A | 28A | 21A | 19A | 18A | 22A | 40A | 38A |

TABLE 2-continued

| Compound | Conc % | Test organisms | | | | | | | |
|---|---|---|---|---|---|---|---|---|---|
| | | a | b | c | Sal | Ps | Er | Psl | X |
| | 1 | 21A | 21A | 16A | 12A | 11A | 12A | 30A | 25A |
| | 0.1 | 15A | 15A | 13A | 12B | — | +A | 15A | +A |
| (2) | 10 | 26A | 30A | 20A | 18A | 19A | 48A | 36A | 36A |
| | 1 | 23A | 25A | 19A | 18B | 11A | 30A | 30A | 30A |
| | 0.1 | 17A | 20A | 13A | 13B | — | — | 17A | 17A |
| (11) | 10 | 27A | 28A | 19A | 16A | 14A | 32A | 38A | 36A |
| | 1 | 24A | 22A | 16A | 15B | 18C | 26A | 29A | 28A |
| | 0.1 | 19A | 16A | 12A | 11B | — | — | 16A | 14A |
| (16) | 10 | 25A | 28A | 20A | 17A | 15 17C | — | 35A | 35A | 35A |
| | 1 | 22A | 23A | 16A | 16B | (+A) | 30A | 28A | 26A |
| | 0.1 | 17A | 19A | 12A | 11B | — | — | 14A | 13A |
| (4) | 10 | 26A | 28A | 19A | 17A | 14A | 44A | 37A | 35A |
| | 1 | 22A | 22A | 16A | 17B | 15C | 30A | 28A | 27A |
| | 0.1 | 16A | 15A | 11A | 11B | — | 11A | 15A | 11A |

Notes:
A: Completely inhibited
B: Strongly inhibited
C: Slightly inhibited
+: Inhibited, but practically without any inhibition zone
—: Not inhibited
Test organisms:
a: *Staphyllococcus aureus* FDA209P
b: *Bacillus subtilis* IAM1069
c: *Escherichia coli* IAM1239
Sal: *Salmonella typhimurium* IFO12529
Ps: *Pseudomonas aeruginosa* AKV823
Er: *Erwinia aroideae* E-705
Psl: *Pseudomonas lachrymans*
X: *Xanthomonas oryzae*

The compounds of the present invention can be incorporated into such substrates or bases as aqueous surfactant solutions, toiletries, textile products, paper articles, paints and deodorants. The resulting compositions can be used for attaining cleanliness of living tissues and living environments by applying or spraying the compositions thereto or thereon. The concentration of the farnesylacetic acid amide compounds in the substrates or bases is generally 0.01 to 20% by weight. When they are added to toiletries or foods during manufacturing processes, they act also as preservatives. The compounds of the present invention can be formulated in appropriate forms of agricultural and horticultural pesticides according to methods conventional in the art. More detailedly, solutions, suspensions, emulsifiable concentrates, emulsions, wettable powders, dusts and granules can be prepared by dissolving, dispersing or suspending the compounds in inert carriers, mixing the compounds with inert carriers, impregnating inert carriers with the compounds or making inert carriers adsorb the compounds, if necessary with the addition of appropriate adjuvants. The carriers may be solids such as powdered cellulose, clay, sand, calcium carbonate, calcium phosphate and chemical fertilizers or liquids such as water, alcohols, hydrocarbons and chlorinated hydrocarbons. In wetting, solubilizing, emulsifying or dispersing, such adjuvants as surfactants, gelatin, casein and gum arabic may be used. The concentration of the active components in the resulting formulations is not critical but generally in the range of 0.5 to 20% by weight for solid formulations such as dusts and granules or of 10 to 50% by weight for liquid formulations such as emulsifiable concentrates and suspensions. The solid formulations are applied generally in amounts of 30 to 200 grams per 10 areas. The liquid formulations are generally diluted to concentrations of 10 ppm to 2% by weight prior to application.

The invention will appear more fully from the examples which follow. These examples are set forth by way of illustration only and it will be understood that the invention is not to be construed as limited thereby either in spirit or in scope as many modifications both in materials and in methods will be apparent from this disclosure to those skilled in the art.

EXAMPLE 1

A three-necked flask equipped with a stirrer, a reflux condenser and a thermometer was charged with 132 g of farnesylacetic acid, 140 g of triphenylphosphine and 500 ml of carbon tetrachloride, and the contents were heated under reflux of carbon tetrachloride for 4 hours. The reaction mixture was filtered to remove a formed solid matter, the carbon tetrachloride distilled off, 500 ml of n-hexane added, the mixture ice-cooled and the crystalline precipitate filtered off. The n-hexane was then distilled off, leaving 146 g of crude farnesylacetyl chloride.

A solution of 12.3 g of N,N-dimethylethylenediamine in 50 cc of ether was placed in a three-necked flask equipped with a stirrer, a dropping funnel and a thermometer. Then 37 g of the above-mentioned farnesylacetyl chloride was added dropwise at 5° to 10° C. After completion of the dropping, the reaction was continued at room temperature for an hour. After the reaction, 70 g of a 10% aqueous solution of sodium hydroxide was added, the aqueous layer was separated from the ether layer and extracted with ether, and the ether extract was combined with the ether layer. The ether was distilled off from the ether solution. The residue was subjected to preparative liquid chromatography (Waters Associates, Prep LC/System 500), which gave 38.5 g of N,N-dimethyl-N'-farnesylacetylethylenediamine (1). The structure was identified by proton NMR and mass spectrometry (M.S.). The NMR data are shown below.

F—CH$_2$CONHCH$_2$CH$_2$N(CH$_3$)$_2$     [Compound (1)]

(δ in CCl$_4$ 90 MHz)

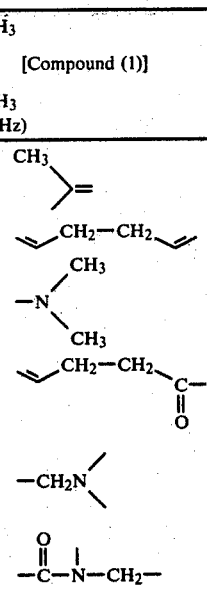

| | | | |
|---|---|---|---|
| 1.50–1.65 | (m) | 12H | CH$_3$\\>= |
| 1.87–2.05 | (m) | 8H | CH$_2$—CH$_2$ |
| 2.16 | (s) | } 10H | —N(CH$_3$)$_2$, CH$_2$—CH$_2$—C(=O)— |
| 2.05–2.22 | (m) | | |
| 2.23, 2.30, 2.37 | (t) | 2H | —CH$_2$N< |
| 3.09, 3.16, 3.22, 3.29 | (q) | 2H | —C(=O)—N(H)—CH$_2$— |
| 4.90–5.17 | (b) | 3H | =CH— |
| 6.56, 6.63, 6.70 | (t) | 1H | —C(=O)—N(H)— |

Water (210 g) was added to 27.3 g of the above, N,N-dimethyl-N'-farnesylacetylethylenediamine and then 74.85 ml of 1 N hydrochloric acid was added dropwise to prepare an aqueous solution of the corresponding hydrochloride. The aqueous solution was yellow and transparent and foamed on stirring.

EXAMPLES 2–6

Using farnesylacetyl chloride and amines specified in Table 3 and following the procedure of Example 1, there were synthesized several farnesylacetamides each containing an amine nitrogen and hydrochlorides thereof. The results are summarized in Table 3.

TABLE 3

| | Starting materials | | Product | | | | |
|---|---|---|---|---|---|---|---|
| Example No. | Farnesyl acetyl chloride (g) | Amine (g) | Compound and yield (g) | Appearance | Method of purification | Method of identification | Description of aqueous solution of hydrochloride |
| 2 | 31.2 | H$_2$NCH$_2$CH$_2$CH$_2$N(CH$_3$)$_2$ (10.2) | Compound (8) (25.8) | Yellow liquid | Preparative liquid chromatography | Proton NMR and M.S. | Pale yellow, transparent liquid (10%) |
| 3 | 31.2 | H$_2$NCH$_2$CH$_2$N(C$_2$H$_5$)$_2$ (11.6) | Compound (3) (18.0) | Yellow liquid | Column chromatography | Proton NMR and M.S. | Pale yellow, transparent liquid (10%) |
| 4 | 31.2 | H$_2$NCH$_2$CH$_2$CH$_2$N(C$_2$H$_5$)$_2$ (12.4) | Compound (10) (19.2) | Yellow liquid | Column chromatography | Proton NMR and M.S. | Pale yellow, transparent liquid (10%) |
| 5 | 31.2 | CH$_3$HNCH$_2$CH$_2$N(CH$_3$)$_2$ (10.2) | Compound (15) (18.2) | Yellow liquid | Column chromatography | Proton NMR and M.S. | Pale yellow, transparent liquid (10%) |
| 6 | 19.8 | H$_2$NCH$_2$C(CH$_3$)$_2$—N(CH$_3$)$_2$ (7.3) | Compound (24) (12.4) | Yellow liquid | Column chromatography | Proton NMR and M.S. | Pale yellow, transparent liquid (10%) |

NMR data

Example 2 [Compound (8)]

(δ in CDCl$_3$ 90MHz)

| | | |
|---|---|---|
| 1.60 (s), 1.67 | (s) | 14H |
| 1.90–2.15 | (m) | 8H |
| 2.24 | (s) | (6H) |
| 2.15–2.26 | (m) | (4H) } 12H |
| 2.30, 2.37, 2.44 | (t) | (2H) |
| 3.20, 3.27, 3.33, 3.40 | (q) | 2H |
| 4.95–5.25 | (m) | 3H |
| 6.95–7.20 | (m) | 1H |

Example 3 [Compound (3)]

(δ in CDCl$_3$ 90MHz)

| | | |
|---|---|---|
| 0.94, 1.03, 1.10 | (t) | 6H |
| 1.61 (b,s) and 1.69 | (s) | 12H |
| 1.93–2.17 | (m) | 8H |
| 2.17–2.35 | (m) | 4H |
| 2.40–2.70 | (m) | 6H |
| 3.21, 3.28, 3.34, 3.41 | (q) | 2H |
| 5.00–5.28 | (m) | 3H |
| 6.40–6.70 | (b) | 1H |

Example 4 [Compound (10)]

(δ CDCl$_3$ 90MHz)

| | | |
|---|---|---|
| 0.94, 1.03, 1.10 | (t) | 6H |
| 1.50–1.75 | (m) | 14H |
| 1.90–2.13 | (m) | 8H |

TABLE 3-continued

| | | |
|---|---|---|
| 2.13–2.30 | (m) | 4H |
| 2.33–2.65 | (m) | 6H |
| 3.22, 3.29, 3.36, 3.42 | (q) | 2H |
| 4.95–5.25 | (m) | 3H |
| 7.25–7.55 | (b) | 1H |

Example 5 [Compound (15)]
(δ CDCl$_3$ 90MHz)

| | | |
|---|---|---|
| 1.54 (s) and 1.61 | (s) | 12H |
| 1.87–2.10 | (m) | 8H |
| 2.22 | (s) | (6H) ⎫ |
| 2.15–2.30 | (m) | (4H) ⎬ 12H |
| (2.31), 2.38, 2.45 | (t) | (2H) ⎭ |
| 2.87, 2.94 | (d) | 3H |
| 3.05–3.50 | (m) | 2H |
| 4.90–5.20 | (m) | 3H |

Example 6 [Compound (24)]
(δ in CDCl$_3$ 90MHz)

| | | |
|---|---|---|
| 1.34 | (s) | 6H |
| 1.63 (s) and 1.70 | (s) | 12H |
| 1.95–2.20 | (m) | 8H |
| 2.37 | (s) | (6H) ⎫ |
| 2.20–2.50 | (m) | (4H) ⎬ 10H |
| 4.06 | (s) | 2H |
| 5.00–5.30 | (m) | 3H |
| 6.40 | (b, s) | 1H |

EXAMPLE 7

Methyl farnesylacetate (42.0 g) and 12.5 g of 2-piperazinylethylamine were placed in a three-necked flask equipped with a thermometer and a stirrer. The contents were heated at 160° C. for five hours to carry out the reaction. The reaction mixture was treated by the procedure of Example 1. The same preparative liquid chromatography as in Example 1 gave 13.2 g of the product as a pale brown liquid. A 10% aqueous solution of the hydrochloride of the farnesylacetamide compound so produced was yellow and transparent. The NMR data for the product were as follows:

F—CH$_2$CONHCH$_2$CH$_2$N⟨NH⟩  [Compound (19)]

(δ in CDCl$_3$ 90 MHz)

| | | |
|---|---|---|
| 1.60 (s) and 1.68 | (s) | 12H |
| 1.83 | (s) | 1H |
| 1.93–2.17 | (m) | 8H |
| 2.17–2.33 | (m) | 4H |
| 2.33–2.60 | (m) | 6H |
| 2.83, 2.88, 2.93 | (t) | 4H |
| 3.24, 3.30, 3.37, 3.43 | | 2H |
| 4.98–5.25 | (m) | 3H |
| 6.00–6.30 | (b) | 1H |

EXAMPLE 8

A three-necked flask equipped with a thermometer, a reflux condenser and a gas inlet tube was charged with 10 g of N,N-dimethyl-N'-farnesylacetylethylenediamine prepared by the procedure of Example 1 and 100 ml of acetonitrile. The contents were refluxed for 6 hours while methyl chloride was introduced. Thereafter, the methyl chloride and acetonitrile were distilled off and the remaining product was purified by column chromatography to give 8.6 g of farnesylacetylaminoethyltrimethylammonium chloride. The product was identified by proton NMR and elemental analysis. The NMR data were as follows:

F—CH$_2$CONHCH$_2$CH$_2$N(CH$_3$)$_3^\oplus$ · Cl$^\ominus$  [Compound (21)]

(δ in CDCl$_3$ 90MHz)

| | | | |
|---|---|---|---|
| 1.56 and 1.62 | (s) | CH$_3$\C=C/ | 12H |
| 1.85–2.10 | (b) | \CH$_2$—CH$_2$/ | 8H |
| 2.15–2.30 | (b) | \CH$_2$—CH$_2$—C(=O)/ | 4H |
| 3.38 | (s) | —N$^\oplus$(CH$_3$)$_3$ | 9H |
| 3.55–3.90 | (m) | H—NCH$_2$— and —CH$_2$—N$^\oplus$— | 4H |
| 4.90–5.20 | (m) | \CH= | |
| 8.50 | (b, s) | H—C(=O)—N— | |

EXAMPLE 9

Dosage Form Suited for Oral Administration

The ingredients shown below were mixed and the resulting mixture was formed into tablets using a tableting machine.

| Ingredient | Weight (mg) per tablet |
|---|---|
| Hydrochloride of compound (1) | 100 |
| Corn starch | 50 |
| Crystalline cellulose | 100 |
| Carboxymethylcellulose | 50 |
| Total | 300 |

EXAMPLE 10

Capsules for Oral Administration

The following ingredients were mixed by a conventional method and the resulting mixture was packed in hard gelatin capsules.

| Ingredient | Weight (mg) per capsule |
|---|---|
| Hydrochloride of compound (8) | 50 |
| Magnesium metasilicate aluminate | 150 |
| Corn starch | 100 |
| Total | 300 |

EXAMPLE 11

Injectable Solution

Compound (1) in the form of hydrochloride (5 g) and 10 g of glucose were dissolved in distilled water for injection and the total amount was made 500 ml.

What is claimed is:

1. A farnesylacetic acid amide compound of the formula

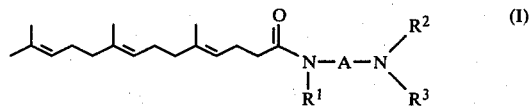

wherein A is a straight or branched alkylene group having from 2 to 10 carbon atoms,
$R^1$ is a hydrogen atom or a lower alkyl group, and
$R^2$ and $R^3$ are the same or different and each is a hydrogen atom, $C_1$–$C_{10}$ alkyl, $C_5$ or $C_6$ cycloalkyl, methylcyclohexyl, $C_2$–$C_{15}$ alkenyl, phenyl, tolyl, xylyl, benzyl or phenethyl,
or either of $R^2$ and $R^3$ forms, together with A, a piperidine or pyrrolidine ring which contains the nitrogen atom lying therebetween,
or $R^2$ and $R^3$ form, together with the adjacent nitrogen atom a piperidine, pyrrolidine piperazine or N-methylpiperazine ring; and pharmaceutically acceptable salts thereof.

2. A farnesylacetic acid amide compound as claimed in claim 1, which is in the form of hydrochloride.

3. A farnesylacetic acid amide compound as claimed in claim 1, which is in the form of quaternary ammonium salt.

4. A farnesylacetic acid amide compound as claimed in claim 1, wherein, in formula (I), A is an alkylene group represented by the formula

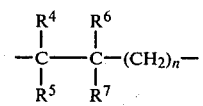

wherein $R^4$, $R^5$, $R^6$ and $R^7$ are each a hydrogen atom or a lower alkyl group or any one of them forms, together with $R^2$ or $R^3$, a piperidine or pyrrolidine ring, and n is an integer of 0 or 1.

5. A farnesylacetic acid amide compound as claimed in claim 1, wherein, in formula (I), $R^1$ is a hydrogen atom or a methyl group and $R^2$ and $R^3$ are each independently a hydrogen atom or a methyl or ethyl group.

6. A farnesylacetic acid amide compound as claimed in claim 1, wherein $R^1$ is a hydrogen atom or a methyl group and $R^2$ and $R^3$ form, together with the adjacent nitrogen atom, a piperidine, pyrrolidine or piperazine ring.

7. The compound according to claim 5, which is N,N-dimethyl-N'-farnesylacetylethylenediamine and its pharmaceutically acceptable salts.

8. The compound according to claim 5, which is N,N-diethyl-N'-farnesylacetylethylenediamine and its pharmaceutically acceptable salts.

9. The compound according to claim 5, which is N,N-dimethyl-N'-farnesylacetylpropylenediamine and its pharmaceutically acceptable salts.

10. The compound according to claim 5, which is N,N-diethyl-N'-farnesylacetylpropylenediamine and its pharmaceutically acceptable salts.

* * * * *